US012608808B2

(12) United States Patent
Kang et al.

(10) Patent No.: US 12,608,808 B2
(45) Date of Patent: Apr. 21, 2026

(54) CORONARY ARTERY STENT PREDICTION METHOD, DEVICE, AND RECORDING MEDIUM USING DEEP LEARNING BASED ON ULTRASOUND IMAGE

(71) Applicant: ATHEROSOFT, Inc., Seoul (KR)

(72) Inventors: Soo Jin Kang, Seoul (KR); June Goo Lee, Seoul (KR); Hyun Seok Min, Suwon-si (KR); Hyung Joo Cho, Seoul (KR)

(73) Assignee: ATHEROSOFT, Inc., Seoul (KR)

( * ) Notice: Subject to any disclaimer, the term of this patent is extended or adjusted under 35 U.S.C. 154(b) by 424 days.

(21) Appl. No.: 18/255,780

(22) PCT Filed: Dec. 2, 2021

(86) PCT No.: PCT/KR2021/018114
§ 371 (c)(1),
(2) Date: Jun. 2, 2023

(87) PCT Pub. No.: WO2022/119350
PCT Pub. Date: Jun. 9, 2022

(65) Prior Publication Data
US 2024/0112343 A1      Apr. 4, 2024

(30) Foreign Application Priority Data
Dec. 20, 2020      (KR) ........................ 10-2020-0166973

(51) Int. Cl.
*G06T 7/00*          (2017.01)
*G06T 7/11*          (2017.01)
(Continued)

(52) U.S. Cl.
CPC .............. *G06T 7/0016* (2013.01); *G06T 7/11* (2017.01); *G06T 7/12* (2017.01); *G06T 7/174* (2017.01);
(Continued)

(58) Field of Classification Search
None
See application file for complete search history.

(56) References Cited

U.S. PATENT DOCUMENTS

| 2016/0267243 A1 | 9/2016 | Zhao et al. |
| 2018/0085170 A1 | 3/2018 | Gopinath |
(Continued)

FOREIGN PATENT DOCUMENTS

| EP | 2 977 922 B1 | 3/2019 |
| KR | 10-2017-0104065 A | 9/2017 |
(Continued)

OTHER PUBLICATIONS

Dong, Pengfei, et al. "Simulation-Driven Machine Learning for Predicting Stent Expansion in Calcified Coronary Artery." Applied Sciences 10.17 (2020): 5820. (Year: 2020).*
(Continued)

*Primary Examiner* — Sean M Conner
(74) *Attorney, Agent, or Firm* — Oblon, McClelland, Maier & Neustadt, L.L.P.

(57) ABSTRACT

A deep learning-based stent prediction method including: setting as a region of interest, a region in which a procedure is to be performed among blood vessel regions of a target patient, and obtaining a first intravascular ultrasound (IVUS) image, which is a preprocedural IVUS image of the region of interest, obtaining a plurality of first IVUS cross-sectional images into which the first IVUS image is divided at predetermined intervals, extracting feature information about procedure information of the target patient, obtaining mask image information in which a blood vessel boundary and an inner wall boundary are distinguished from each other, with respect to the plurality of first IVUS cross-sectional images, and predicting progress of a stent procedure containing a postprocedural area of a stent for the target patient, by inputting, into an artificial intelligence model, the
(Continued)

FIRST IVUS IMAGE 10,10'

SECOND IVUS IMAGE 20

OBTAIN FIRST PROCESSED IVUS IMAGE 30 plurality of first IVUS cross-sectional images, the feature information, and the mask image information.

6 Claims, 10 Drawing Sheets

(51) Int. Cl.

| | |
|---|---|
| *G06T 7/12* | (2017.01) |
| *G06T 7/174* | (2017.01) |
| *G06T 7/62* | (2017.01) |
| *G06V 10/764* | (2022.01) |
| *G06V 10/774* | (2022.01) |
| *G16H 50/20* | (2018.01) |
| *G16H 50/50* | (2018.01) |

(52) U.S. Cl.
CPC .............. *G06T 7/62* (2017.01); *G06V 10/764* (2022.01); *G06V 10/774* (2022.01); *G16H 50/20* (2018.01); *G16H 50/50* (2018.01); *G06T 2207/10132* (2013.01); *G06T 2207/20081* (2013.01); *G06T 2207/30048* (2013.01); *G06T 2207/30096* (2013.01); *G06T 2207/30101* (2013.01); *G06V 2201/031* (2022.01)

(56) References Cited

U.S. PATENT DOCUMENTS

| | | | |
|---|---|---|---|
| 2020/0294659 A1 | 9/2020 | Gopinath et al. | |
| 2021/0042927 A1* | 2/2021 | Amis | ................... G06T 7/0012 |
| 2021/0090249 A1 | 3/2021 | Choi et al. | |
| 2021/0259777 A1* | 8/2021 | Chatzizisis | ............ G16H 30/40 |
| 2023/0389799 A1 | 12/2023 | Gopinath et al. | |
| 2024/0057870 A1 | 2/2024 | Gopinath et al. | |
| 2024/0130793 A1 | 4/2024 | Gopinath | |

FOREIGN PATENT DOCUMENTS

| | | |
|---|---|---|
| KR | 10-2019-0083185 A | 7/2019 |
| KR | 10-2009840 B1 | 8/2019 |
| KR | 10-2019-0125596 A | 11/2019 |
| KR | 10-2020-0026136 A | 3/2020 |

OTHER PUBLICATIONS

Fujino, Akiko, et al. "A new optical coherence tomography-based calcium scoring system to predict stent underexpansion." EuroIntervention 13.18 (2018): e2182-e2189. (Year: 2018).*

Gharaibeh, Yazan, et al. "Co-registration of pre-and post-stent intravascular OCT images for validation of finite element model simulation of stent expansion." Proceedings of SPIE—the International Society for Optical Engineering. vol. 11317. 2020. (Year: 2020).*

Min, Hyun-Seok et al., "Prediction of Coronary Stent Underexpansion by Pre-Procedural Intravascular Ultrasound-Based Deep Learning," JACC: Cardiovascular interventions, vol. 14, No. 9, 2021, pp. 1021-1029, XP086561790.

Extended European Search Report issued Sep. 20, 202 in European Patent Application No. 21901038.6, 8 pages.

International Search Report mailed on Mar. 8, 2022 in PCT/KR2021/018114 filed on Dec. 2, 2021 (3 pages).

* cited by examiner

120

| | |
|---|---|
| IMAGE PROCESSING UNIT | 121 |
| FEATURE EXTRACTION UNIT | 122 |
| MASK IMAGE OBTAINING UNIT | 123 |
| STENT PREDICTION UNIT | 124 |
| TREATMENT TECHNIQUE DETERMINATION UNIT | 125 |

FIRST PROCESSED IVUS IMAGE 30

FIG. 8

CORONARY ARTERY STENT PREDICTION METHOD, DEVICE, AND RECORDING MEDIUM USING DEEP LEARNING BASED ON ULTRASOUND IMAGE

CROSS REFERENCE TO RELATED APPLICATIONS

This application is a National Stage entry under 35 U.S.C. § 371 of PCT/KR2021/018114, filed on Dec. 2, 2021, and claims priority to Korean Patent Application No. 10-2020-0166973, filed on Dec. 2, 2020. The entire contents of both are incorporated herein by reference.

TECHNICAL FIELD

The present disclosure relates to an artificial intelligence (AI) system for simulating functions of a human brain, such as recognition or judgment, by using a deep learning algorithm, and applications of the AI system.

More particularly, the present disclosure relates to a method, device, and recording medium for predicting incomplete expansion of a coronary stent through a deep learning algorithm based on an ultrasound image of a coronary artery, and determining an optimal treatment technique for the coronary artery.

BACKGROUND ART

Recently, artificial intelligence systems that simulate human-level intelligence have been used in various fields. An artificial intelligence system enables machines to become smart by learning and making decisions on their own, compared to an existing rule-based smart system. As the artificial intelligence system is more frequently used, the recognition rate of the artificial intelligence system is improved and accurately understands a user's preference, and accordingly, the existing rule-based smart systems have gradually been replaced with deep-learning-based artificial intelligence systems. The artificial intelligence technology includes machine learning (e.g., deep learning) and element technologies utilizing machine learning.

Intravascular ultrasound (IVUS) is a clinical examination method used to recognize morphological features of coronary artery lesions, observe arteriosclerosis, and optimize a stent procedure. A drug-eluting stent insertion procedure for a coronary artery stenosis has been established as a standard coronary artery stenosis treatment, but there is a risk of surgical complications such as a stent thrombosis or restenosis. Known major causes of stent complications include a sign of incomplete stent expansion immediately after a procedure, residual stenosis of reference vessel, vascular dissection, and tissue separation. In particular, there is an issue that the risk of stent failure (e.g., restenosis, stent thrombosis) increases when a stent area is not sufficiently secured. Thus, there is an increasing need for a process of optimizing coronary artery stent procedure such that a stent area satisfies a preset reference value.

DESCRIPTION OF EMBODIMENTS

Technical Problem

Embodiments of the present disclosure provide a method, device, and recording medium for predicting incomplete expansion of a coronary stent through a deep learning model based on an intravascular ultrasound image (IVUS), and accordingly determining an optimal treatment technique for a coronary artery.

However, this objective is merely illustrative, and the scope of the present disclosure is not limited thereto.

Solution to Problem

A deep learning-based stent prediction method according to an embodiment of the present disclosure includes: setting, as a region of interest, a region in which a procedure is to be performed, among blood vessel regions of a target patient, and obtaining a first intravascular ultrasound (IVUS) image, which is a preprocedural IVUS image of the region of interest; obtaining a plurality of first IVUS cross-sectional images into which the first IVUS image is divided at predetermined intervals; extracting feature information about procedure information about the target patient; obtaining mask image information in which a blood vessel boundary and an inner wall boundary are distinguished from each other, with respect to the plurality of first IVUS cross-sectional images; and predicting progress of a stent procedure including a postprocedural area of a stent for the target patient, by inputting, into an artificial intelligence model, the plurality of first IVUS cross-sectional images, the feature information, and the mask image information.

The deep learning-based stent prediction method may further include obtaining clinical features of the patient, and the predicting of the progress of the stent procedure may include predicting the postprocedural area of the stent by additionally inputting the clinical features into the artificial intelligence model.

The predicting of the progress of the stent procedure may include: calculating the postprocedural area of the stent for the target patient; and determining whether the stent is to be incompletely expanded, by comparing the postprocedural area of the stent with a preset reference value.

The predicting of the progress of the stent procedure may include determining, based on the postprocedural area of the stent and whether the stent is to be incompletely expanded, a treatment technique regarding whether to perform the stent procedure on the target patient, and the determining of the treatment technique may include, based on determining to perform the stent procedure, outputting stent guide information including a diameter, a length, a balloon pressure of the stent, and based on determining not to perform the stent procedure, outputting a procedure other than the stent procedure.

The deep learning-based stent prediction method may further include training the artificial intelligence model based on training data including first processed IVUS images of a plurality of previous patients, and the first processed IVUS images may be obtained by: registering second reference IVUS images, which are postprocedural IVUS images of the plurality of previous patients, with respect to first reference IVUS images, which are preprocedural IVUS images of the plurality of previous patients; and labeling the first reference IVUS images with stent area values of the second reference IVUS images.

The training may include: extracting, based on the first processed IVUS images and stent procedure information of the plurality of previous patients, reference feature information about the stent procedure information; obtaining, based on at least one of the first reference IVUS images and the first processed IVUS images, reference mask image information in which a blood vessel boundary and an inner wall boundary are distinguished from each other; and training the artificial intelligence model by using, as training data, the reference feature information and the reference mask image information.

Meanwhile, a recording medium according to an embodiment of the present disclosure may be a computer-readable recording medium having recorded thereon a program for executing the stent prediction method according to the above-described embodiments.

A stent prediction device according to an embodiment of the present disclosure includes: an image processing unit configured to obtain a first IVUS image, which is a preprocedural IVUS image of a region of interest, which is a region among blood vessel regions of a target patient in which a procedure is to be performed, and a plurality of first IVUS cross-sectional images into which the first IVUS image is divided at predetermined intervals; a feature extraction unit configured to extract feature information about procedure information about the target patient; a mask image obtaining unit configured to obtain mask image information in which a blood vessel boundary and an inner wall boundary are distinguished from each other, with respect to the plurality of first IVUS cross-sectional images; and a stent prediction unit configured to predict progress of a stent procedure including a postprocedural expansion area of a stent for the target patient, by inputting, into an artificial intelligence model, the plurality of first IVUS cross-sectional images, the feature information, and the mask image information.

Other aspects, features, and advantages than those described above will become clear from the following detailed description, claims, and drawings for carrying out the present disclosure.

Advantageous Effects of Disclosure

According to an embodiment of the present disclosure, by using a preprocedural intravascular ultrasound (IVUS) image, incomplete expansion of a coronary stent may be predicted, and an optimal treatment technique according to a result of the predicting, such as pretreatment before stent insertion, may be provided.

In addition, according to embodiments of the present disclosure, by using a machine learning algorithm based on pre- and postprocedural IVUS images of an entire blood vessel, it is possible to quickly and accurately predict incomplete expansion of a stent and a risk thereof, and provide an optimized standard for a stent procedure corresponding to a result of the predicting.

In addition, according to embodiments of the present disclosure, there is provided a technique for optimizing a stent procedure by using only pre- and postprocedural IVUS images without the need for a high-resolution optical image or tissue analysis image examination, such that examination time and cost may be reduced.

However, the scope of the present disclosure is not limited by these effects.

BRIEF DESCRIPTION OF DRAWINGS

FIG. 8 is a diagram for describing an input preprocessing operation and an input/output relationship according to an embodiment of the present disclosure.

MODE OF DISCLOSURE

Figure 1:
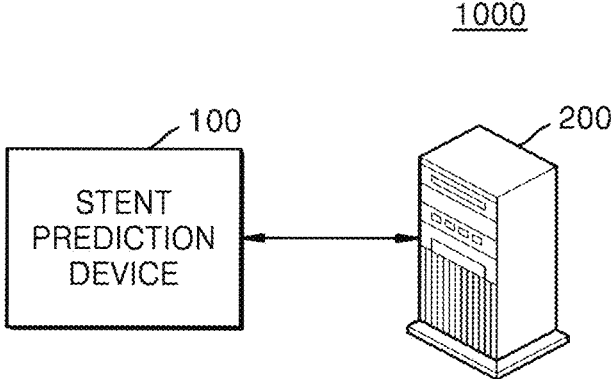
FIG. 1 is a system diagram illustrating a stent prediction system according to an embodiment of the present disclosure.

Hereinafter, various embodiments of the present disclosure will be described with reference to the accompanying drawings. Various embodiments of the present disclosure may be variously modified and may have various embodiments, and particular embodiments are illustrated in the drawings and detailed descriptions related to the embodiments are described. However, this is not intended to limit various embodiments of the present disclosure to particular modes of practice, and it is to be appreciated that all changes, equivalents, and/or substitutes that do not depart from the spirit and technical scope of various embodiments of the present disclosure are encompassed in the present disclosure. With regard to the description of the drawings, similar reference numerals are used to refer to similar elements.

As used in various embodiments of the present disclosure, the expressions "include", "may include", and other conjugates refer to the existence of a corresponding disclosed function, operation, or constituent element, and do not limit one or more additional functions, operations, or constituent elements. In addition, as used in various embodiments of the present disclosure, the terms "include", "have", and other conjugates are intended merely to denote a certain feature, numeral, step, operation, element, component, or a combination thereof, and should not be construed to initially exclude the existence of or a possibility of addition of one or more other features, numerals, steps, operations, elements, components, or combinations thereof.

As used in various embodiments of the present disclosure, expressions such as "or" include any and all combinations of the listed words. For example, "A or B" may include A, may include B, or may include both A and B.

As used in various embodiments of the present disclosure, expressions such as "first" or "second" may modify various components of various embodiments, but do not limit the components. For example, the expressions do not limit the order and/or importance of the components. The expressions may be used to distinguish one component from another.

It should be understood that, when it is described that an element is "connected" or "coupled" to another element, the first element may be directly connected or coupled to the second element, and a third element may be connected or coupled between the first and second elements. On the other hand, it should be understood that, when it is described that a first element is "directly connected" or "directly coupled" to a second element, no further element is present between the first element and the second element.

As used in embodiments of the present disclosure, terms such as "module", "unit", "part", etc., denote a unit of a component that performs at least one function or operation, and may be implemented as hardware or software or a combination of hardware and software. In addition, a plurality of "modules", "units", "parts", etc. may be integrated into at least one module or chip to be implemented as at least one processor, except for cases in which each of them needs to be implemented as separate particular hardware.

The terms used in various embodiments of the present disclosure are used only to describe a particular embodiment, and are not intended to limit the various embodiments of the present disclosure. A singular expression may include a plural expression unless they are definitely different in a context.

Unless otherwise defined, all terms, including technical and scientific terms, used herein have the same meaning as commonly understood by those of skill in the art to which the present disclosure pertains based on an understanding of the present disclosure.

Terms, such as those defined in commonly used dictionaries, are to be interpreted as having a meaning that is consistent with their meaning in the context of the relevant art and various embodiments of the present disclosure, and are not to be interpreted in an idealized or overly formal sense unless expressly so defined herein.

Hereinafter, various embodiments of the present disclosure will be described in detail with reference to the accompanying drawings.

FIG. 1 is a system diagram illustrating a stent prediction system 1000 according to an embodiment of the present disclosure.

Referring to FIG. 1, the stent prediction system 1000 of the present disclosure may include a stent prediction device 100 and a server 200.

The stent prediction device 100 is a device for predicting a postprocedural stent area and whether a stent is to be incompletely expanded, with respect to a patient's coronary artery, and recommending and determining an optimal treatment technique according to a result of the predicting. The stent prediction device 100 may predict a postprocedural stent area and incomplete expansion, based on a preprocedural intravascular ultrasound (IVUS) image of a region of interest of the coronary artery of the patient in which a coronary stent is inserted, and recommend and determine, according to a result of the predicting, a patient-specific optimal treatment technique for a coronary artery disease. In detail, the stent prediction device 100 may predict postprocedural progress of a stent procedure, based on an input preprocedural IVUS image, by using an artificial intelligence model.

The server 200 is at least one external server for training and updating an artificial intelligence model and performing prediction through the artificial intelligence model.

The server 200 according to an embodiment of the present disclosure may include an artificial intelligence model for predicting progress of a stent procedure for a patient and determining an optimal treatment technique.

In this case, the artificial intelligence model may be trained by using 'first processed IVUS images' obtained by registering pre- and postprocedural IVUS images of a plurality of previous patients. In detail, the 'first processed IVUS images' may be obtained by registering second reference IVUS images, which are postprocedural IVUS images, with respect to first reference IVUS images, which are preprocedural IVUS images of the plurality of previous patients, and labeling, concurrently with the registering, the first reference IVUS images with stent area values of the second reference IVUS images.

Accordingly, when a first IVUS image, which is a preprocedural IVUS image of a target patient for which progress of a stent procedure is to be predicted, and various pieces of feature information about the procedure and the patient are input to the artificial intelligence model of the present disclosure, the progress of the stent procedure including a postprocedural stent expansion area may be predicted. In this case, the feature information may include morphological features, procedural features, and clinical features of a blood vessel included in the first IVUS image, but is not limited thereto. This will be described in detailed below with reference to the relevant drawings.

Although FIG. 1 illustrates that the stent prediction device 100 and the server 200 are implemented as separate components, they may be implemented as one component according to an embodiment of the present disclosure. That is, according to an embodiment, the stent prediction device 100 may be an on-device artificial intelligence device that directly trains and updates an artificial intelligence model.

Figure 2:
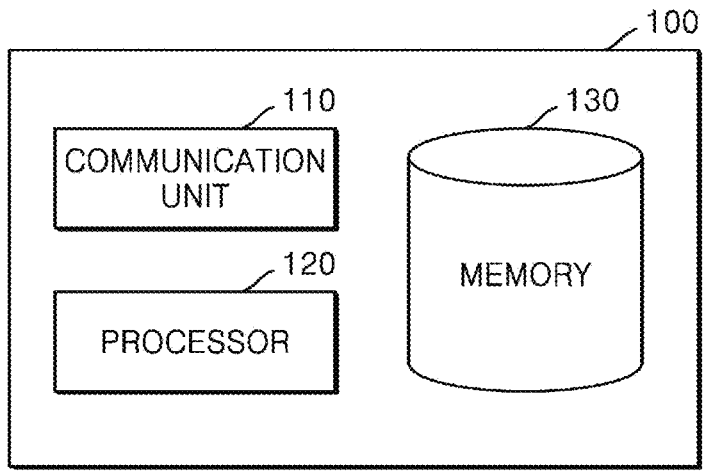
FIG. 2 is a simple block diagram for describing components of a stent prediction device according to an embodiment of the present disclosure.

FIG. 2 is a simple block diagram for describing components of the stent prediction device 100 according to an embodiment of the present disclosure.

Referring to FIG. 2, the stent prediction device 100 may include a communication unit 110, a processor 120, and a memory 130.

The communication unit 110 may be configured to perform communication with various types of external devices according to various types of communication schemes. The communication unit 110 may include at least one of a Wi-Fi chip, a Bluetooth chip, a wireless communication chip, and a near-field communication (NFC) chip. The processor 120 may communicate with the server 200 or various types of external devices by using the communication unit 110.

In particular, when the Wi-Fi chip or Bluetooth chip is used, various pieces of connection information, such as a service set identifier (SSID) or a session key, may be first transmitted and received, and various pieces of information may be then transmitted and received after a communication connection is established by using the connection information. The wireless communication chip refers to a chip that performs communication according to various communication standards, such as Institute of Electrical and Electronics Engineers (IEEE), Zigbee, $3^{rd}$ Generation (3G), $3^{rd}$ Generation Partnership Project (3GPP), or Long-Term Evolution (LTE). The NFC chip refers to a chip that operates in an NFC scheme using a 13.56 MHz band among various radio-frequency identification (RFID) frequency bands, such as 135 kHz, 13.56 MHz, 433 MHz, 860 MHz to 960 MHz, 2.45 GHz, or the like.

The processor 120 is configured to control the overall operation of the stent prediction device 100. In detail, the processor 120 controls the overall operation of the stent prediction device 100 by using various programs stored in the memory 130 of the stent prediction device 100. For example, the processor 120 may include a central processing unit (CPU), random-access memory (RAM), read-only memory (ROM), and a system bus. Here, the ROM is a component in which a command set for system booting is stored, and the CPU copies an operating system stored in the memory of the stent prediction device 100 to the RAM according to a command stored in the ROM, and executes an operating system (OS) to boot a system. When the booting is completed, the CPU may copy various applications stored in the memory 130 to the RAM, and execute the applications to perform various operations. Although it is described above that the processor 120 includes only one CPU, the processor 120 may be implemented with a plurality of CPUs (or digital signal processors (DSPs), systems on a chip (SoC), etc.).

According to an embodiment of the present disclosure, the processor 120 may be implemented as a DSP, a microprocessor, or a time controller (TCON) for processing a digital signal. However, the present disclosure is not limited thereto, and the processor 120 may include one or more of a CPU, a microcontroller unit (MCU), a microprocessing unit (MPU), a controller, an application processor (AP), a communication processor (CP), or an Advanced Reduced Instruction Set Computer (RISC) Machines (ARM) processor, or may be defined as the corresponding term. In addition, the processor 120 may be implemented as an SoC or large-scale integration (LSI) in which a processing algorithm is embedded, or may be implemented as a field-programmable gate array (FPGA).

A detailed configuration and function of the processor 120 will be described in more detail below with reference to FIGS. 3 to 5.

The memory 130 may store various pieces of data for the overall operation of the stent prediction device 100, such as a program for the processor 120 to perform processing or control. The memory 130 may temporarily or permanently store all types of data processed by the stent prediction system 1000. The memory 130 may store a plurality of application programs (or applications) executable by the stent prediction device 100, and pieces of data and instructions for the operation of the stent prediction device 100. At least some of the application programs may be downloaded from an external server through wireless communication.

In addition, at least some of the application programs may exist on the stent prediction device 100 from the time of release for the basic functions of the stent prediction device 100. The application programs may be stored in the memory 130 to be executed by the processor 120 to perform an operation (or a function) of the stent prediction device 100. In particular, the memory 130 may be implemented as an internal memory included in the processor 120, such as ROM or RAM, or may be implemented as a separate memory from the processor 120.

Although not illustrated, the stent prediction device 100 may further include an image obtaining unit and an image processing unit. The image obtaining unit may obtain IVUS image data before and after a stent procedure, through various sources. For example, the image obtaining unit may be implemented as a commercially available scanner to obtain an IVUS image by scanning the inside of a coronary artery. Image data obtained through the image obtaining unit may be processed by the image processing unit.

The image processing unit may process the image data obtained through the image obtaining unit. The image processing unit may perform various image processing operations, such as decoding, scaling, noise filtering, frame rate conversion, or resolution conversion, on the image data. The image obtaining unit or the image processing unit may transmit an image obtained by each component, to each component of the processor 120 of FIG. 3 to be described below, such that subsequent image processing is performed.

In addition, although not illustrated in FIG. 2, the stent prediction device 100 may include other components within a range in which a stent prediction method of the present disclosure may be easily implemented.

Figure 3:
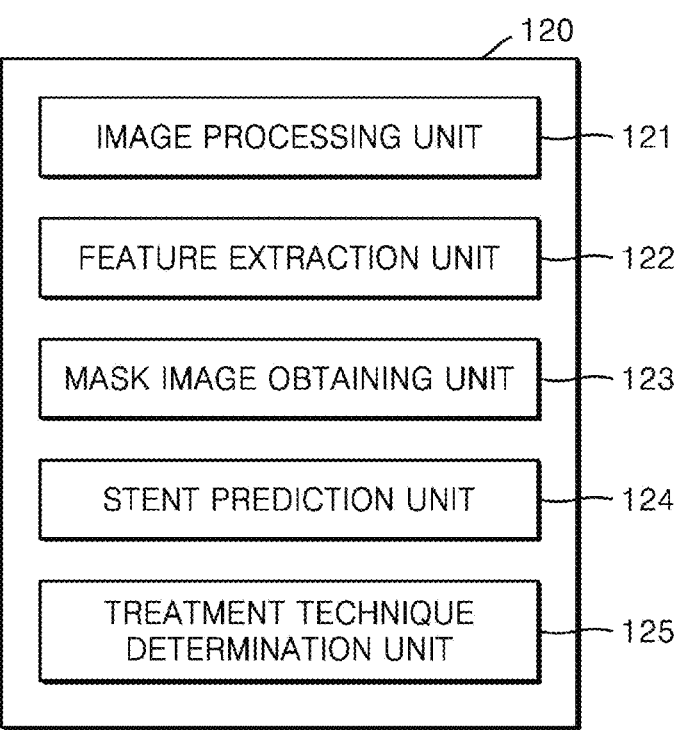
FIG. 3 is a block diagram for describing components of a processor according to an embodiment of the present disclosure.

FIG. 3 is a block diagram for describing components of the processor 120 according to an embodiment of the present disclosure.

Referring to FIG. 3, the processor 120 of the present disclosure may include an image processing unit 121, a feature extraction unit 122, a mask image obtaining unit 123, a stent prediction unit 124, and a treatment technique determination unit 125. Hereinafter, the stent prediction unit 124 and the treatment technique determination unit 125 may be referred to as output units 124 and 125, respectively.

According to an embodiment of the present disclosure, the image processing unit 121, the feature extraction unit 122, the mask image obtaining unit 123, the stent prediction unit 124, and the treatment technique determination unit 125 may be implemented as respective software modules stored in the memory 130 included in the stent prediction device 100 to be executed by the processor 120. Each of the software modules may perform one or more functions and operations described herein. In addition, the components may be implemented as separate modules or may be implemented as one module.

Meanwhile, according to another embodiment of the present disclosure, the stent prediction unit 124 and the treatment technique determination unit 125 are components corresponding to an output unit of the stent prediction device 100, and may be a component included in a processor (not shown) of the server 200. In this case, the server 200 may receive, from the stent prediction device 100, input data such as a first processed IVUS image obtained by processing a preprocedural IVUS image of a patient, morphological information and procedural features of a blood vessel included in the first processed IVUS image, mask image information, and clinical features of the patient, predict, based on the received input data, progress of a stent procedure, and provide a guide for an optimal procedure technique for each patient.

A detailed operation of each component of the processor 120 will be described in detail below with reference to the drawings.

Hereinafter, the stent prediction method of the present disclosure will be described with reference to FIGS. 4, 5, and 3.

Figure 4:
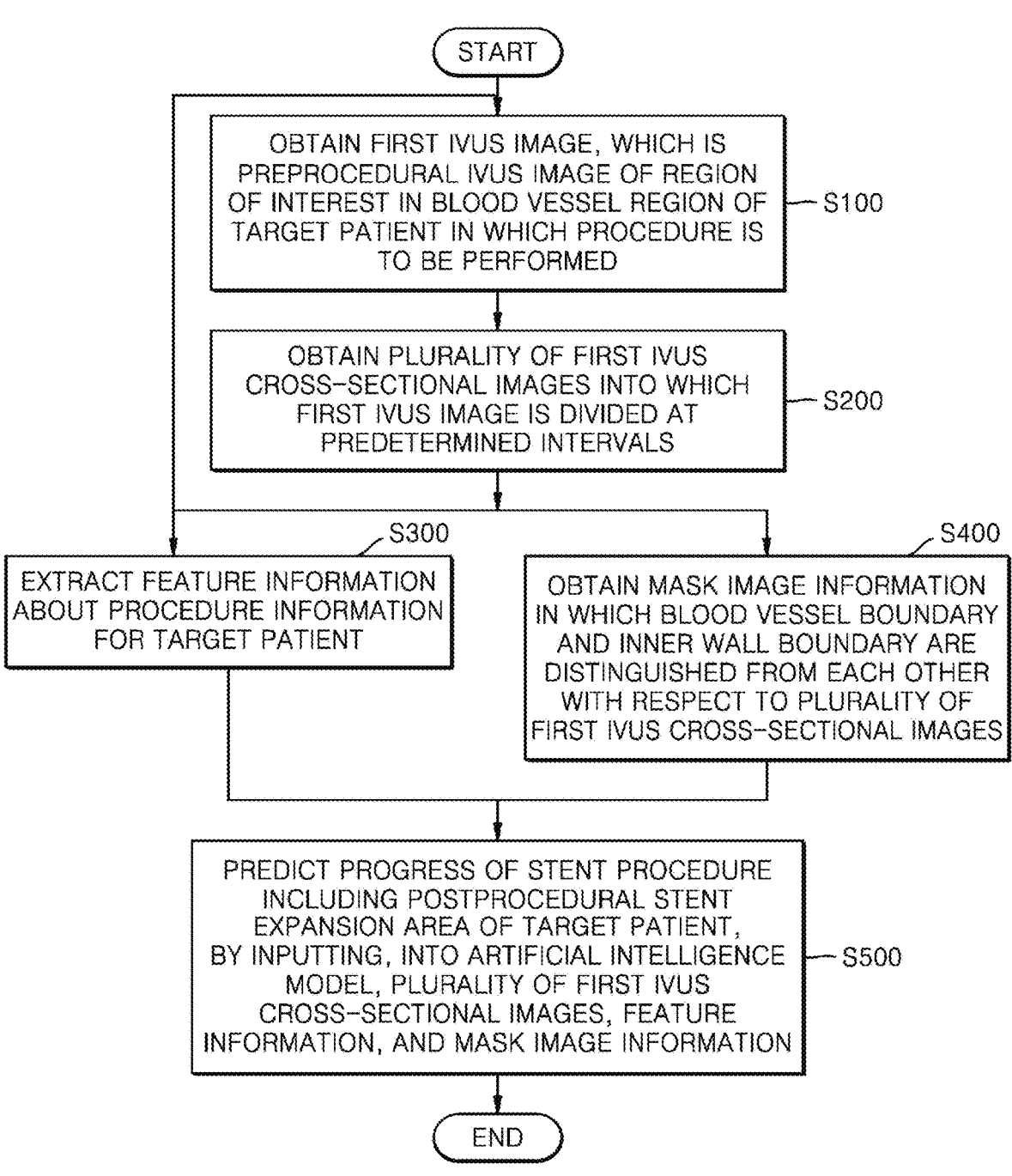
FIG. 4 is a flowchart illustrating a stent prediction method according to an embodiment of the present disclosure.

FIG. 4 is a flowchart illustrating a stent prediction method according to an embodiment of the present disclosure.

The image processing unit 121 of the present disclosure may set, as a region of interest, a region in a blood vessel region of a target patient in which a procedure is to be performed, and obtain a first IVUS image, which is a preprocedural IVUS image of the region of interest (S100). The region of interest is a segment of the blood vessel region requiring insertion of a stent, and may be set based on IVUS image findings and the like.

Thereafter, the image processing unit 121 may obtain a plurality of first IVUS cross-sectional images into which the first IVUS image is divided at predetermined intervals (S200). As such, the stent prediction method of the present disclosure may provide a customized preemptive treatment method by more accurately predicting progress of a stent procedure by using cross-sectional images of an entire region of interest of a preprocedural blood vessel image rather than a particular cross-section, and cross-sectional images of an entire blood vessel rather than only a particular part such as a boundary of the blood vessel. An operation of the image processing unit 121 will be described in more detail below with reference to FIG. 6.

The feature extraction unit 122 extracts feature information about procedure information for the target patient (S300). As illustrated in the present drawing, in operation S300, the first IVUS image that has passed operation S100 and/or operation S200 may be used, but information about stent procedures that have been performed or are to be performed on a plurality of previous patients separately from the first IVUS image may be used. An operation of the feature extraction unit 122 will be described in more detail below with reference to FIG. 7.

The mask image obtaining unit 123 obtains mask image information in which a blood vessel boundary and an inner wall boundary are distinguished from each other with respect to the plurality of first IVUS cross-sectional images (S400). An operation of the mask image obtaining unit 123 will be described in more detail below with reference to FIG. 8.

As illustrated in the present drawing, the extracting of the feature information (S300) and the obtaining of the mask image information (S400) may be concurrently performed. In other words, the predicting (S500) performed by the output units 124 and 125 to be described below may be performed by using only the feature information about the procedure information obtained by the feature extraction unit 122, and may be performed by using both the feature information and the mask image information obtained by the mask image obtaining unit 123. Operations S300 and S400 may be simultaneously performed, operation S400 may be performed after operation S300, or only operation S300 may be performed and operation S400 may not be performed according to an embodiment. However, in a case in which both the mask image information and the feature information are used as input data in the predicting of the progress of the stent procedure (S500), there is an advantage in that the prediction accuracy may be improved.

The stent prediction unit 124 predicts the progress of the stent procedure including a postprocedural stent expansion area for the target patient, by inputting, into an artificial intelligence model, at least one of the plurality of first IVUS cross-sectional images, the feature information, and the mask image information (S500). In predicting the progress of the stent procedure, the processor 120 may obtain clinical features of the patient, and for example, this operation may be performed by the feature extraction unit 122. The clinical features of the patient may also be input into the artificial intelligence model to predict the postprocedural stent area.

The predicting of the progress of the stent procedure (S500) includes calculating a postprocedural stent area for the target patient, and determining whether the stent is to be incompletely expanded, by comparing the postprocedural stent area with a preset reference value. For example, the reference value may be about 5.5 mm$^2$, and it may be determined, based on the predicted postprocedural stent area being less than about 5.5 mm$^2$, that the stent is to be incompletely expanded, and it may be determined, based on the predicted postprocedural stent area being greater than or equal to about 5.5 mm$^2$ that the stent is not to be incompletely expanded.

Based on the postprocedural stent area and whether the stent is to be incompletely expanded, the treatment technique determination unit 125 may determine a treatment technique regarding whether to perform the stent procedure. For example, when the stent prediction unit 124 determines that the stent is to be incompletely expanded, a modified design for a stent procedure or another procedure technique may be proposed and provided.

For example, the determining of the treatment technique may include outputting, based on determining to perform the stent procedure, stent guide information including a diameter, a length, and a stent balloon pressure of a stent, and outputting, based on determining not to perform the stent procedure, a procedure method other than the stent procedure. The other procedure method may include, for example, a preprocedural atherectomy.

Figure 5:
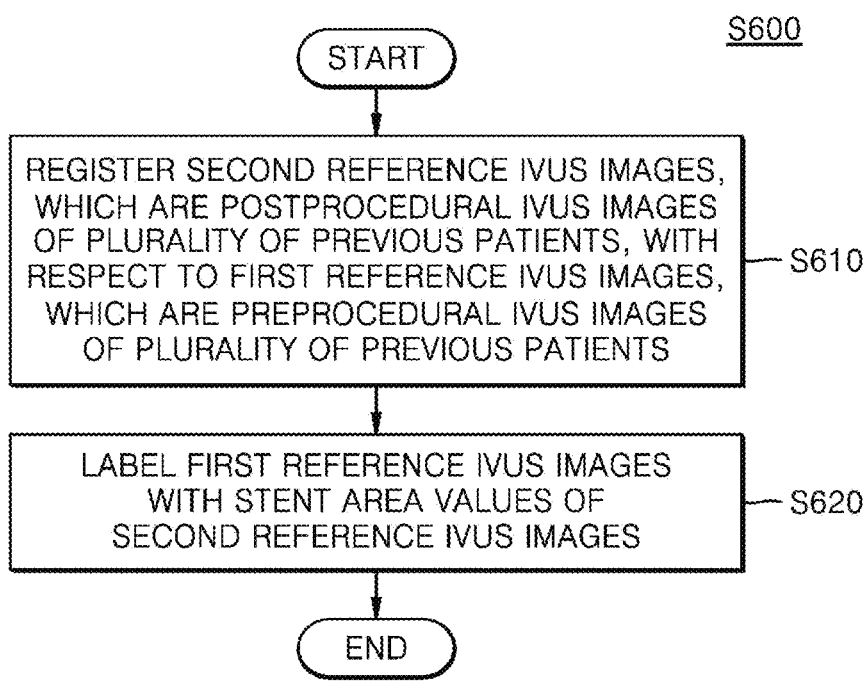
FIG. 5 is a flowchart for describing an operation of training an artificial intelligence model in a stent prediction method according to an embodiment of the present disclosure.

FIG. 5 is a flowchart for describing an operation of training an artificial intelligence model in a stent prediction method according to an embodiment of the present disclosure. A deep learning-based stent prediction method of the present disclosure further includes training an artificial intelligence model based on training data including first processed IVUS images of a plurality of previous patients (S600). Operation S600 may be performed by a training unit 1210 (see FIG. 10) of a processor to be described below or by the processor (not shown) of the server 200. The first processed IVUS images generated in operation S600 may be generated by operations to be described below.

Second reference IVUS images, which are postprocedural IVUS images of the plurality of previous patients, are registered with respect to first reference IVUS images, which are preprocedural IVUS images of the plurality of previous patients (S610).

Thereafter, the first reference IVUS images are labeled with stent area values of the second reference IVUS images (S620). Here, the first and second reference IVUS images may be a plurality of cross-sectional images that are results of dividing at preset intervals. Generation of the training data will be described in more detail below with reference to FIG. 6.

The training of the artificial intelligence model (S600) may further include operations to be described below, and this may be applied in the same principle as input and output operations by the stent prediction method of the present disclosure.

Based on the first processed IVUS images and stent procedure information of the plurality of previous patients obtained as described above, reference feature information about the stent procedure information may be extracted. Meanwhile, based on at least one of the first reference IVUS images and the first processed IVUS images, reference mask image information in which a blood vessel boundary and an inner wall boundary are distinguished from each other may be obtained.

Thereafter, the artificial intelligence model may be trained by using, as training data, the reference feature information and the reference mask image information together with the first processed IVUS images.

Figure 6:
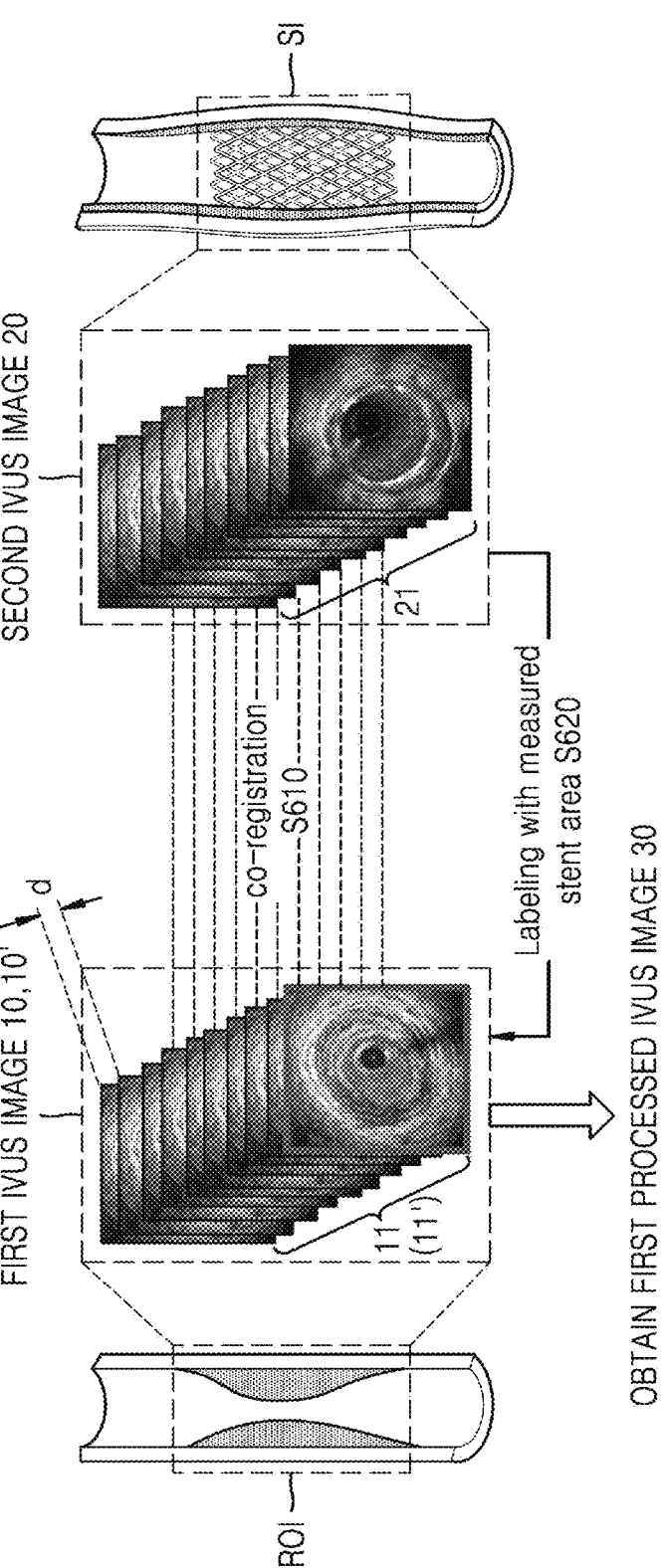
FIG. 6 is a diagram for describing an input preprocessing operation according to an embodiment of the present disclosure.

FIG. 6 is a diagram for describing an input preprocessing operation according to an embodiment of the present disclosure, and is a diagram for describing a method of obtaining a first processed IVUS image as input data and training data for training an artificial intelligence model of the present disclosure. The operation of FIG. 6 may be performed by the image processing unit 121 of the processor 120 or by the processor (not shown) of the server 200.

Referring to FIG. 6, the image processing unit 121 may obtain, as training data, a first processed IVUS image 30, based on a first IVUS image 10, which is a preprocedural IVUS image of a patient, and a second IVUS image 20, which is a postprocedural IVUS image. According to an embodiment, the first processed IVUS image 30 is input data necessary for generating output data for predicting progress of a stent procedure of a target patient, and may be an image that is not registered with respect to the second IVUS image 20.

The image processing unit 121 sets, as a region of interest ROI, a stent insertion segment of a blood vessel region of the target patient, and obtains the first IVUS image 10 of the region of interest ROI. Thereafter, the first IVUS image 10 is divided at predetermined intervals to obtain a plurality of first IVUS cross-sectional images 11. Here, the predetermined interval d may be, for example, about 0.5 mm, but is not limited thereto. The first IVUS image 10 including the plurality of first IVUS cross-sectional images 11 may be input data for stent prediction according to the present disclosure.

Hereinafter, a method of obtaining the first processed IVUS image 30 as training data will be described. The following operations may be performed by the processing unit 121 or the training unit 1210 (see FIG. 10). In generating the training data, the first IVUS image 10 may be a first reference IVUS image 10 of a plurality of previous patients.

First, a first reference IVUS image 10', which is a pre-procedural IVUS image of the region of interest ROI in which a procedure is to be performed, among blood vessel regions of the plurality of previous patients is obtained. Thereafter, a plurality of first reference IVUS cross-sectional images 11' into which the first reference IVUS image 10' is divided at the predetermined intervals d are obtained. The same operations may be performed on the second reference IVUS image 20, which is a postprocedural IVUS image. The second reference IVUS image 20 is an IVUS image of a stent region SI in which a stent procedure has been performed, which corresponds to the region of interest ROI of the blood vessel of the patient before the procedure. Here, second reference IVUS cross-sectional images 21 may be obtained by dividing the second reference IVUS image at the same intervals d as the first reference IVUS image.

Thereafter, the plurality of second reference IVUS cross-sectional images 21 are registered with respect to the plurality of first reference IVUS cross-sectional images 11' (S610) (see FIG. 5). Each of the registered first reference IVUS cross-sectional images 11' is labeled with a stent area value measured in each of the plurality of second reference IVUS cross-sectional images 21 corresponding to each segment position (S620) (see FIG. 5). Here, the registering and the labeling may be concurrently performed to finally obtain the first processed IVUS image 30.

Figure 7:
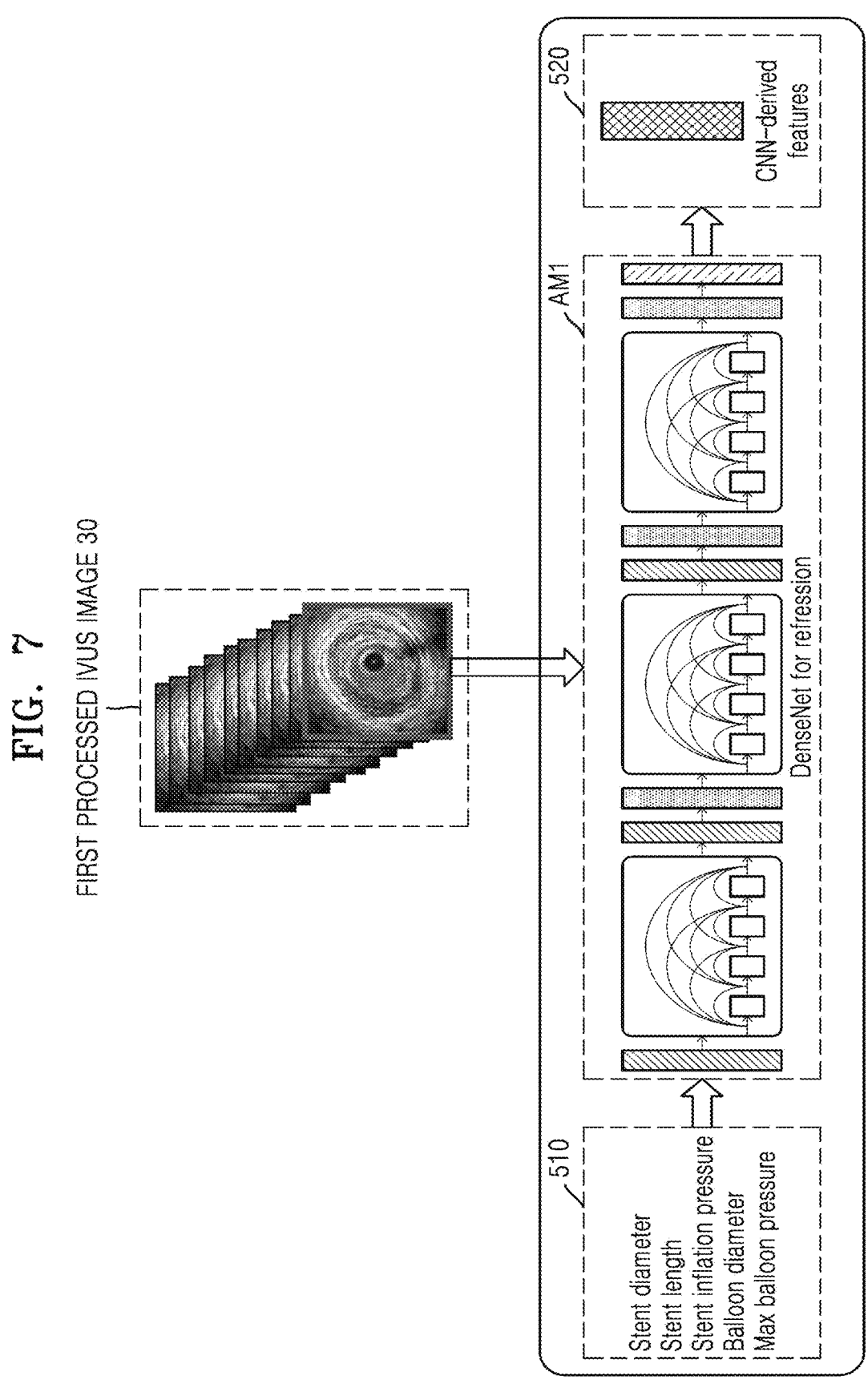
FIG. 7 is a diagram for describing an input preprocessing operation according to another embodiment of the present disclosure.

FIG. 7 is a diagram for describing an input preprocessing operation according to another embodiment of the present disclosure, and is a diagram for describing a method of extracting feature information of the present disclosure. The following operations may be performed by the feature extraction unit 122 of the processor 120 or by the processor (not shown) of the server 200.

The feature extraction unit 122 may extract feature information 520 by inputting, into a first artificial intelligence model AM1, the first processed IVUS image 30 generated by the image processing unit 121, and stent procedure information 510. The stent procedure information 510 may include information about stent procedures that have been performed on a plurality of previous patients, and information about a stent procedure to be performed on a target patient. In detail, the stent procedure information 510 may include various pieces of information about stent procedures, such as a stent diameter, a stent length, a stent inflation pressure, a balloon diameter, or a maximum balloon pressure.

The first artificial intelligence model AM1 may employ a Densely Connected Convolutional Networks (DenseNet) model having significantly excellent performance among convolutional neural network (CNN)-based deep convolutional techniques, and may perform a regression operation, but the technique of the first artificial intelligence model AM1 is not limited thereto. The first artificial intelligence model AM1 may be trained by using the first processed IVUS image 30 and the stent procedure information 510, and accordingly, feature information (e.g., a feature map) may be extracted and updated.

Figure 8:
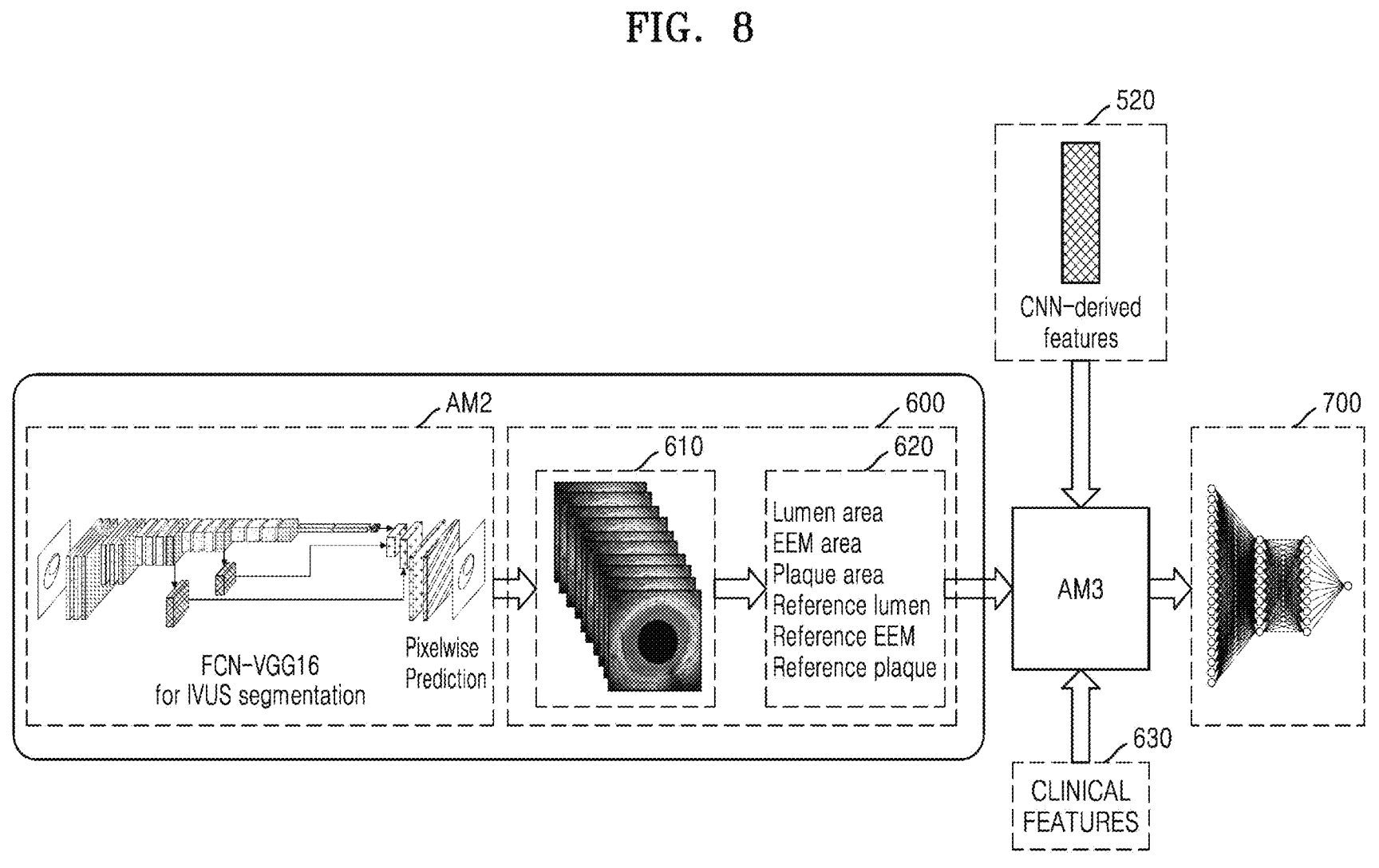

FIG. 8 is a diagram for describing an input preprocessing operation and an input/output relationship according to an embodiment of the present disclosure. The following operations may be performed by the mask image obtaining unit 122 and the output units 124 and 125 of the processor 120, or by the processor (not shown) of the server 200.

The mask image obtaining unit 123 may obtain mask image information 600 by using a second artificial intelligence model AM2 (S400). The mask image information 600 may include mask images 610 and morphological information 620 of a blood vessel. The mask images 610 are images obtained by separating/distinguishing a blood vessel boundary or a luminal boundary from the first IVUS image 10, which is a preprocedural IVUS image of the patient, or from the first processed IVUS image 30 obtained by image-processing the first IVUS image 10, and may include a plurality of mask images 610 corresponding to the plurality of first IVUS cross-sectional images 11, respectively. The morphological information 620 of the blood vessel may include a lumen area, an external elastic membrane (EEM) area, a plaque area, and a reference lumen, a reference EEM, and reference plaque value data, and the like, which are obtained from the mask images 610.

Figure 9:
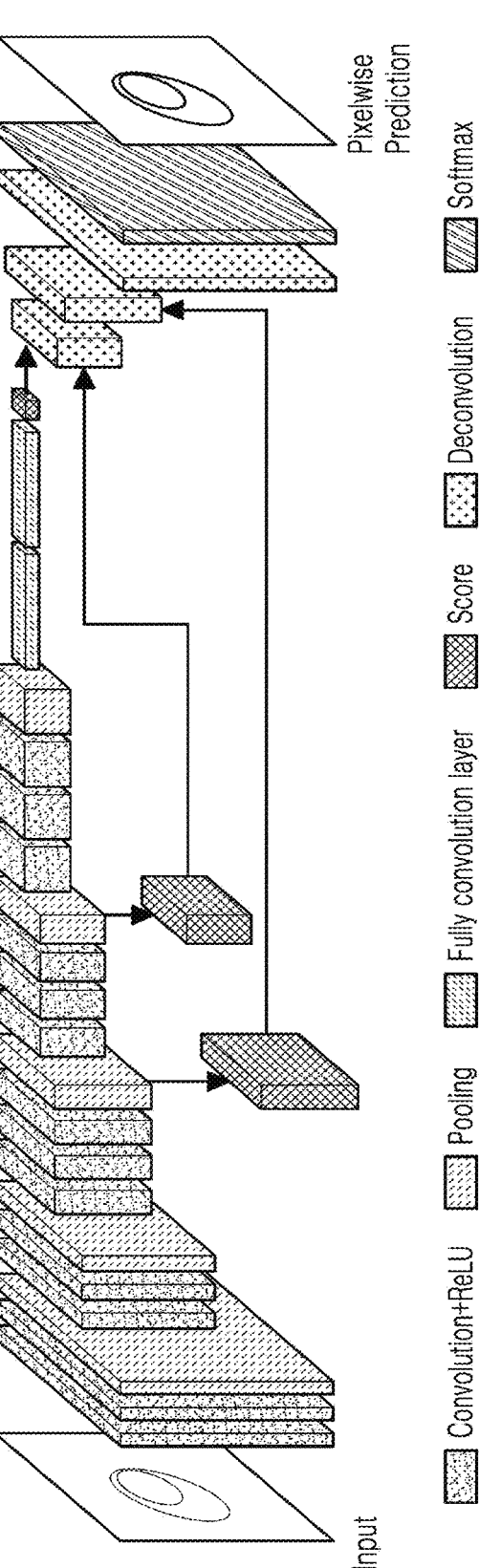
FIG. 9 is a diagram illustrating a configuration of an artificial intelligence model for obtaining a mask image, according to an embodiment of the present disclosure.

Here, the mask images 610 may be generated by segmenting the first IVUS image 10 or the first processed IVUS image 30 by using the second artificial intelligence model AM2, and this will be described with reference to FIG. 9. FIG. 9 is a diagram illustrating the second artificial intelligence model AM2 of the present disclosure in more detail.

Referring to FIG. 9, the second artificial intelligence model AM2 may decompose frames included in an IVUS image by using a fully convolutional network (FCN) that is pre-trained in an ImageNet database. Thereafter, the second artificial intelligence model AM2 applies skip connections to a baseline CNN model in which hierarchical features of convolutional layers of different scales are combined with each other. Here, the baseline CNN model may be, for example, an FCN-VGG16 model. For example, the baseline CNN model may have receptive fields of various sizes through the skip connections, and thus output an output with improved spatial precision. As another example, by combining three predictions of 8, 16, and 32 pixel strides through the skip connections, the second artificial intelligence model AM2 may output an output with improved spatial precision through the FCN-VGG16 model.

Meanwhile, as a preprocessing operation, the second artificial intelligence model AM2 may convert the first IVUS image 10 into an RGB color format by resampling the first IVUS image 10 into a size of 256×256. A center image and a neighboring image having a displacement value different from that of the center image may be merged into a single RGB image, and frame values 0, 1, and 2 may be used as three displacement values, respectively. In another embodiment, as a preprocessing operation, the second artificial intelligence model AM2 may convert the first IVUS image 10 into a multi-channel format by resampling the first IVUS image 10 into a size of 256×256. A center image and a neighboring image having a displacement value different from that of the center image may be merged into a multi-channel image, and frame values 0, 1, and 2 may be used as three displacement values, respectively. In other words, even when segmentation into more diverse classes is performed, frame values may be diversified rather than that dimensions increase.

In detail, the plurality of first IVUS cross-sectional images 11 into which the first IVUS image 10 is divided may be divided into (i) an external membrane including pixels outside an EEM (coded as "0"), (ii) a lumen including pixels within a luminal boundary (coded as "1"), and (iii) a plaque including pixels between the luminal boundary and the EEM (coded as "2"). In order to calibrate pixel dimensions, a grid line may be automatically obtained from the IVUS image, and a cell interval may be calculated.

The second artificial intelligence model AM2, or an FCN-all-at-once-VGG16 model may be trained for each displacement setting by using a preprocessed image pair (e.g., a 24-bit RGB color image and an 8-bit gray mask). As described above, the second artificial intelligence model AM2 may output one mask image 610 by merging three extracted masks.

Referring back to FIG. 8, the output units 124 and 125 of the present disclosure may output output data 700 for predicting progress of a stent procedure of a patient, by inputting, into a third artificial intelligence model AM3, at least one of the feature information 520, the mask image information 600, and clinical features 630 of the patient. Meanwhile, the training unit 1210 (see FIG. 10) of the processor may train and update the third artificial intelligence model AM3 by using, as training data, the feature information 520, the mask image information 600, and the clinical features 630 of the patient. For example, the clinical features 630 may include, but is not limited to, an age, a gender, a body surface area, an involved segment, and involvement of proximal left anterior descending artery (LAD), a vessel type and the like.

The output data 700 may include a postprocedural stent area for the patient and whether a stent is to be incompletely expanded, which are predicted by the stent prediction unit 124, and an optimal treatment technique according thereto. Regarding whether the stent is to be incompletely expanded, it may be determined, based on the predicted postprocedural stent area being less than a preset reference value (e.g., about 5.0 mm²), that the stent is to be incompletely expanded. As an example of the optimal treatment technique, a minimum balloon pressure required for the stent area to be greater than or equal to a minimum area may be determined. For example, when the determined balloon pressure is greater than a predetermined value, a guide for a preprocedural atherectomy may be provided.

Figure 10:
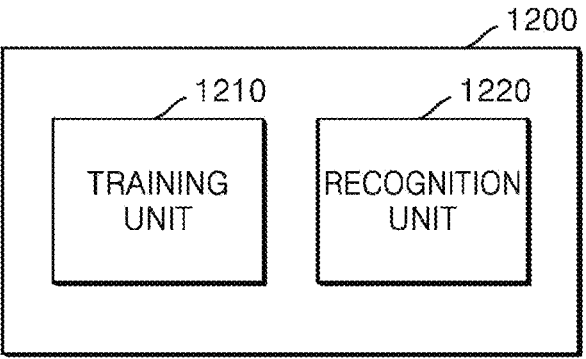
FIG. 10 is a block diagram illustrating a training unit and a recognition unit according to various embodiments of the present disclosure.

FIG. 10 is a block diagram illustrating the training unit 1210 and a recognition unit 1220 according to various embodiments of the present disclosure.

Referring to FIG. 10, a processor 1200 may include at least one of the training unit 1210 and the recognition unit 1220. The processor 1200 of FIG. 10 may correspond to the processor 120 of the stent prediction device 100 of FIG. 2 or the processor (not shown) of the server 200.

The training unit 1210 may generate or train a recognition model having a criterion for determining a certain situation. The training unit 1210 may generate a recognition model having a criterion, by using collected training data.

For example, the training unit 1210 may generate, train, or update an object recognition model having a criterion for determining the type of a lumen of a blood vessel included in an IVUS image, by using various IVUS images (the above-described first IVUS image, second IVUS image, first IVUS cross-sectional image, second IVUS cross-sectional image, and first processed IVUS image) as training data.

As another example, the training unit 1210 may generate, train, or update a model having a criterion for determining a postprocedural stent area for a patient and whether a stent is to be incompletely expanded, by using, as training data, a plurality of first IVUS images, second IVUS images respectively corresponding to the first IVUS images, a first processed IVUS image generated by registering the second IVUS images with respect to the first IVUS images and labeling with stent areas, clinical feature information of the patient corresponding to the IVUS images, stent procedure information, mask image information, and the like.

The recognition unit 1220 may estimate desired data (e.g., the output data 700) by using certain data as input data for the trained recognition model. For example, the recognition unit 1220 may predict progress of a stent procedure and determine and provide an optimal preprocedural treatment technique, by applying, to the trained recognition model, the feature information 520, the mask image information 600, and the clinical features 630, which are extracted based on the first IVUS image 10 and the stent procedure information 510.

At least a portion of the training unit 1210 and at least a portion of the recognition unit 1220 may be implemented as a software module or manufactured in the form of at least one hardware chip, and then mounted on the stent prediction device 100. For example, at least one of the training unit 1210 and the recognition unit 1220 may be manufactured in the form of a dedicated hardware chip for artificial intelligence, or manufactured as a part of an existing general-purpose processor (e.g., a CPU or an AP) or a dedicated graphics processor (e.g., a graphics processing unit (GPU)), and then mounted on various electronic devices or object recognition devices described above. Here, the dedicated hardware chip for artificial intelligence is a dedicated processor specialized in probability calculation, and may quickly process calculation tasks in the field of artificial intelligence such as machine learning, with higher parallel processing performance than that of existing general-purpose processors.

In a case in which the training unit 1210 and the recognition unit 1220 are implemented as software modules (or program modules including instructions), the software modules may be stored in non-transitory computer-readable media. In this case, the software modules may be provided by an operating system (OS) or by a certain application. Alternatively, a part of the software module may be provided by the OS, and the other part may be provided by the certain application.

In this case, the training unit 1210 and the recognition unit 1220 may be mounted on one electronic device, or may be mounted on separate electronic devices, respectively. For example, any one of the training unit 1210 and the recognition unit 1220 may be included in the stent prediction device 100 and the other may be included in the server 200. In addition, the training unit 1210 and the recognition unit 1220 may provide the recognition unit 1220 with information about a model established by the training unit 1210 through wired or wireless communication, and data input to the recognition unit 1220 may be provided as additional training data to the training unit 1210.

Meanwhile, the above-described methods according to various embodiments of the present disclosure may be implemented in the form of an application that may be installed in an existing electronic device.

Meanwhile, according to an embodiment of the present disclosure, the various embodiments described above may be implemented as software including instructions stored in a recording medium that is readable by a computer or similar device, by using software, hardware, or a combination thereof. In some cases, the embodiments described herein may be implemented as a processor. According to software implementation, embodiments such as procedures or functions described herein may be implemented as separate software modules. Each of the software modules may perform one or more functions and operations described herein.

A device-readable recording medium may be provided in the form of a non-transitory computer-readable recording medium. Here, the term 'non-transitory' simply means that the storage medium is a tangible device, and does not include a signal, but this term does not differentiate between where data is semi-permanently stored in the storage medium and where the data is temporarily stored in the storage medium. Here, the non-transitory computer-readable medium refers to a medium that does not store data for a short time like a register, a cache memory, a memory, and the like, but semi-permanently stores data and is readable by a device. Specific examples of non-transitory computer-readable media may include a compact disc (CD), a digital video disc (DVD), a hard disk, a Blu-ray disc, a Universal Serial Bus (USB) drive, a memory card, ROM, and the like.

Although the present disclosure has been described with reference to the embodiments illustrated in the drawings, they are merely exemplary, and it will be understood by one of skill in the art that various modifications and equivalent embodiments may be made therefrom. Therefore, the true technical protection scope of the present disclosure should be determined by the appended claims.

The invention claimed is:

1. A computer-implemented deep learning-based stent prediction method of predicting progress of a stent procedure, the deep learning-based stent prediction method comprising:

setting, by a stent prediction device, as a region of interest, a region in which a procedure is to be performed among blood vessel regions of a target patient, and obtaining a first intravascular ultrasound (IVUS) image, which is a preprocedural IVUS image of the region of interest;

obtaining, by the stent prediction device, a plurality of first IVUS cross-sectional images into which the first IVUS image is divided at predetermined intervals;

extracting, by the stent prediction device, feature information about procedure information of the target patient;

obtaining, by the stent prediction device, mask image information in which a blood vessel boundary and an inner wall boundary are distinguished from each other, with respect to the plurality of first IVUS cross-sectional images; and predicting, by the stent prediction device, progress of a stent procedure comprising a postprocedural area of a stent for the target patient, by inputting, into a deep learning model, the plurality of first IVUS cross-sectional images, the feature information, and the mask image information, wherein the deep learning-based stent prediction method further comprises training the deep learning model by using, as training data, first processed IVUS images of a plurality of previous patients, wherein the first processed IVUS images are obtained by:

registering second reference IVUS images, which are postprocedural IVUS images of the plurality of previous patients, with respect to first reference IVUS images, which are preprocedural IVUS images of the plurality of previous patients; and labeling the first reference IVUS images with stent area values of the second reference IVUS images, and wherein the training comprises:

extracting, based on the first processed IVUS images and stent procedure information of the plurality of previous patients, reference feature information about the stent procedure information;

obtaining, based on at least one of the first reference IVUS images and the first processed IVUS images, reference mask image information in which a blood vessel boundary and an inner wall boundary are distinguished from each other; and training the deep learning model by using the stent area values of the labeled first reference IVUS images and by using, as training data, the reference feature information and the reference mask image information.

2. The deep learning-based stent prediction method of claim 1, further comprising obtaining clinical features of the patient, wherein the predicting of the progress of the stent procedure comprises predicting the postprocedural area of the stent by additionally inputting the clinical features into the deep learning model.

3. The deep learning-based stent prediction method of claim 1, wherein the predicting of the progress of the stent procedure comprises:

calculating the postprocedural area of the stent for the target patient; and determining whether the stent is to be incompletely expanded, by comparing the postprocedural area of the stent with a preset reference value.

4. The deep learning-based stent prediction method of claim 3, wherein the predicting of the progress of the stent procedure comprises determining, based on the postprocedural area of the stent and whether the stent is to be incompletely expanded, a treatment technique regarding whether to perform the stent procedure on the target patient, and the determining of the treatment technique comprises, based on determining to perform the stent procedure, outputting stent guide information comprising a diameter, a length, a balloon pressure of the stent, and based on determining not to perform the stent procedure, outputting a procedure other than the stent procedure.

5. A computer-readable recording medium having recorded thereon a program which when executed by a computer, cause the computer to carry out the steps of the deep learning-based stent prediction method of claim 1.

6. A deep learning-based stent prediction device configured to predict progress of a stent procedure, the device comprising:

an image processing unit configured to obtain a first intravascular ultrasound (IVUS) image, which is a preprocedural IVUS image of a region of interest, which is a region among blood vessel regions of a target patient in which a procedure is to be performed, and a plurality of first IVUS cross-sectional images into which the first IVUS image is divided at predetermined intervals;

a feature extraction unit configured to extract feature information about procedure information about the target patient;

a mask image obtaining unit configured to obtain mask image information in which a blood vessel boundary and an inner wall boundary are distinguished from each other, with respect to the plurality of first IVUS cross-sectional images; and a stent prediction unit configured to predict progress of a stent procedure comprising a postprocedural expansion area of a stent for the target patient, by inputting, into a deep learning model, the plurality of first IVUS cross-sectional images, the feature information, and the mask image information, wherein the stent prediction unit is configured to train the deep learning model by using, as training data, first processed IVUS images of a plurality of previous patients, wherein the first processed IVUS images are obtained by:

registering second reference IVUS images, which are postprocedural IVUS images of the plurality of previous patients, with respect to first reference IVUS images, which are preprocedural IVUS images of the plurality of previous patients; and labeling the first reference IVUS images with stent area values of the second reference IVUS images, and wherein the training comprises:

extracting, based on the first processed IVUS images and stent procedure information of the plurality of previous patients, reference feature information about the stent procedure information;

obtaining, based on at least one of the first reference IVUS images and the first processed IVUS images, reference mask image information in which a blood vessel boundary and an inner wall boundary are distinguished from each other; and training the deep learning model by using the stent area values of the labeled first reference IVUS images and by using, as training data, the reference feature information and the reference mask image information.

* * * * *